United States Patent [19]

Pastan et al.

[11] Patent Number: 5,082,927
[45] Date of Patent: Jan. 21, 1992

[54] SELECTIVELY CYTOTOXIC IL-4-PE40 FUSION PROTEIN

[75] Inventors: Ira Pastan, Potomac; David FitzGerald, Silver Spring; Masato Ogata, Rockville, all of Md.

[73] Assignee: The United States of America as represented by the Department of Health and Human Services, Washington, D.C.

[21] Appl. No.: 351,448

[22] Filed: May 12, 1989

Related U.S. Application Data

[63] Continuation-in-part of Ser. No. 911,227, Sep. 24, 1986, Pat. No. 4,892,827.

[51] Int. Cl.$^5$ .................. C07K 15/00; A61K 37/02; A61K 39/104
[52] U.S. Cl. .................. 530/351; 530/402; 530/403; 530/404; 530/405; 530/406; 530/820; 530/825; 435/69.5; 435/69.52; 435/71.3; 424/85.1; 424/85.2; 424/85.91; 424/92; 935/47; 514/2; 514/8
[58] Field of Search .................. 530/351, 402–406, 530/820, 825; 435/69.5, 69.52, 69.7, 71.3; 424/85.1, 85.2, 85.91, 92

[56] References Cited

U.S. PATENT DOCUMENTS

| 4,545,985 | 10/1985 | Pastan | 514/2 |
| 4,675,382 | 6/1987 | Murphy | 530/350 |
| 4,894,443 | 1/1990 | Greenfield et al. | 530/350 |

FOREIGN PATENT DOCUMENTS 0230107 7/1987 European Pat. Off. .

OTHER PUBLICATIONS

Yokota et al., *PNAS* 83, 1986, pp. 5894–5898.
Chaudhary et al., *Nature*, 339, 1989, pp. 394–397.
Williams *Protein Engineering* 1(6) 1987, pp. 493–498.
Perentesis et al., *PNAS* 85, 1988, pp. 8386–8390.
Olsnes et al., *Pharmac Ther*, vol. 15, 1982, pp. 355–381.
Dr. William Paul, editor, "Fundamental Immunology", 2nd edition, Raven Press, 1989, pp. 634–635, Tables 1 and 2.

*Primary Examiner*—Garnette D. Draper
*Attorney, Agent, or Firm*—Mishrilal Jain

[57] ABSTRACT

The present invention provides a chimeric protein IL4-PE40 which selectively kills IL4 receptor bearing cells. A mutant form of the protein is also provided.

4 Claims, 8 Drawing Sheets

B - Bam HI
E - Eco RI
N - Nde I
P1 - Primer 1
P2 - Primer 2
T7 - T7 late promoter

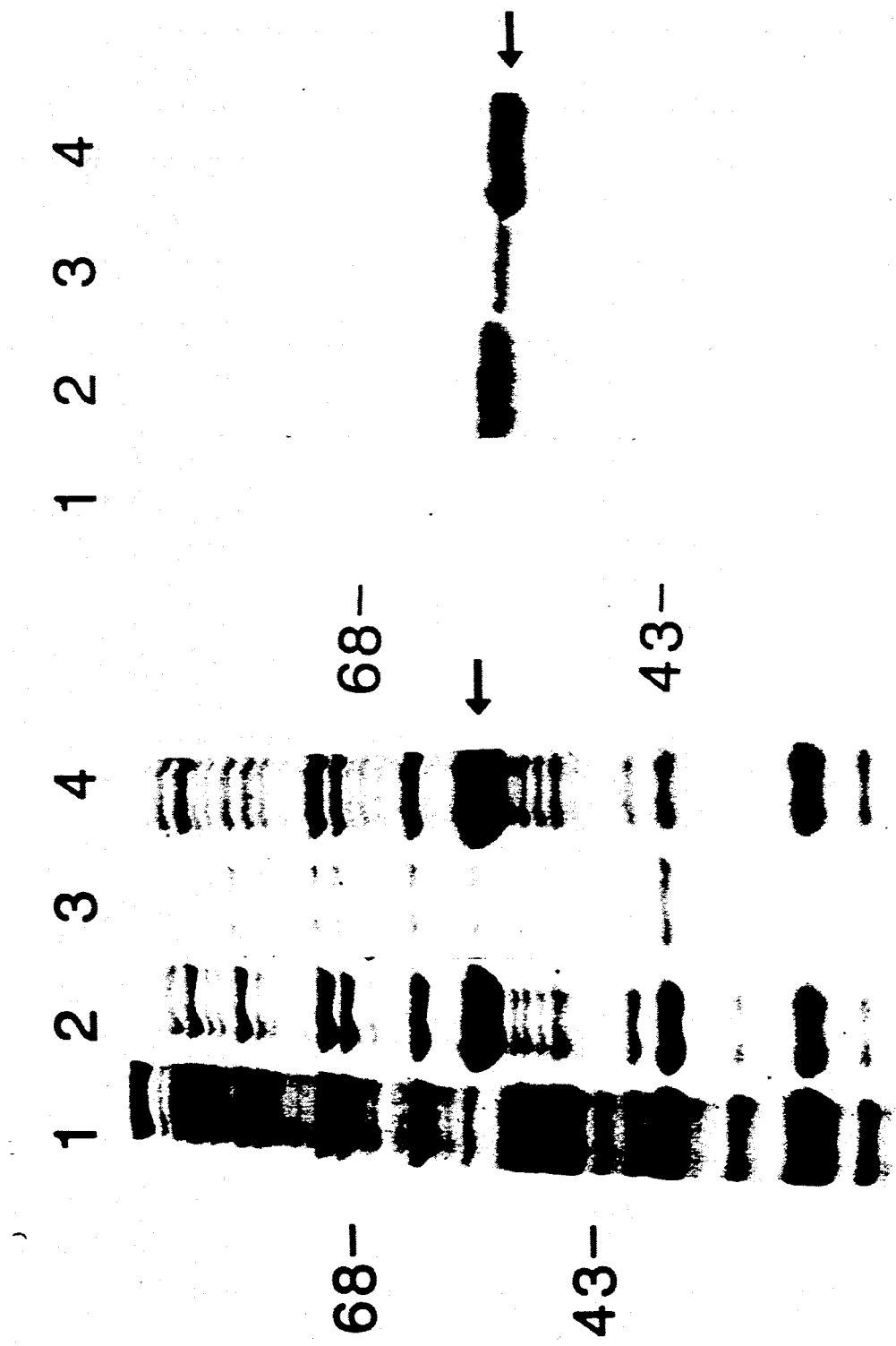

|   1   2 | |   1   2 |
|---|---|

SELECTIVELY CYTOTOXIC IL-4-PE40 FUSION PROTEIN

This is a continuation-in-part of application Ser. No. 06/911,227 filed Sept. 24, 1986 now U.S. Pat.. No. 4,892,827, which is incorporated herein by reference.

The parent application (Ser. No. 06/911,227) teaches the production of recombinant proteins from modified Pseudomonas exotoxin (PE) gene fused with DNA sequences encoding a recognition protein for which a specific receptor exists on the cells. The PE gene was modified to achieve alteration of specific segments or sequences of various domains of the PE molecule while retaining the translocating and ADP ribosylating activities of PE. This was exemplified in the parent application with the construction and expression of an IL-2-PE fusion gene. The present application further illustrates the general principle described in the parent application by synthesizing a recombinant hybrid protein, in particular an IL4-PE40 chimeric toxin which selectively kills cells bearing IL4 receptors.

BRIEF DESCRIPTION OF THE DRAWINGS

Various objects, features and many of the attendant advantages of the invention will be better understood upon a reading of the following detailed description when considered in connection with the accompanying drawings wherein.

Primer 1: 5'-CTTTCTCGAATGTACC<u>CATATG</u>
CATATCCACGGATGCGACAAAAATC-3'

Primer 2: 5'-GTTAAAGCATGGTGGCTCA<u>CAT
ATG</u>CGAGTAATCCATTTGCATG-3'

The bases underlined were changed from that of IL4 to create a NdeI site.

Figure 1A:
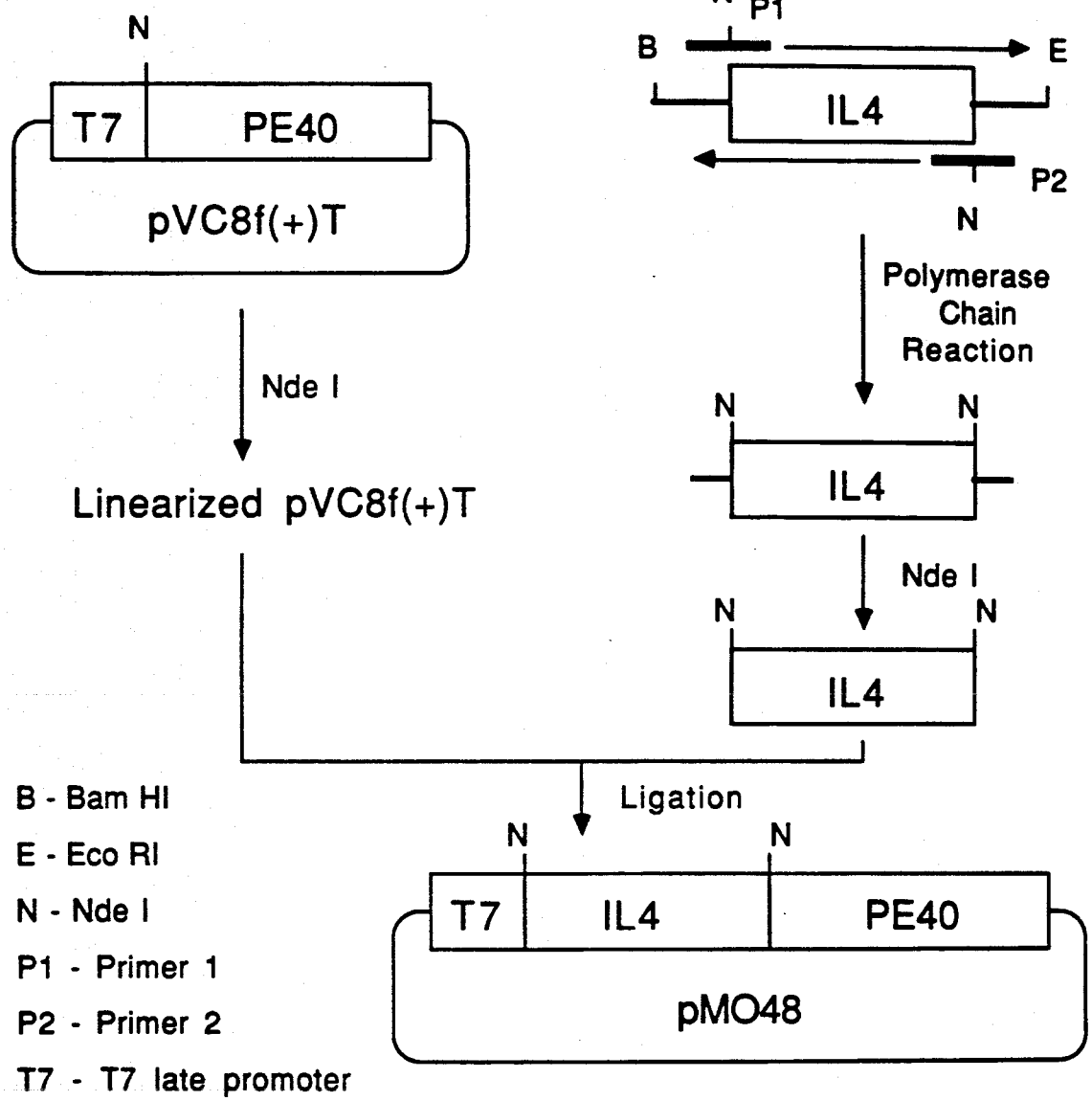
FIG. 1(A) illustrates a schematic construction of expression plasmid pM048, encoding IL4-PE40. Primer sequence.
Figure 1B:
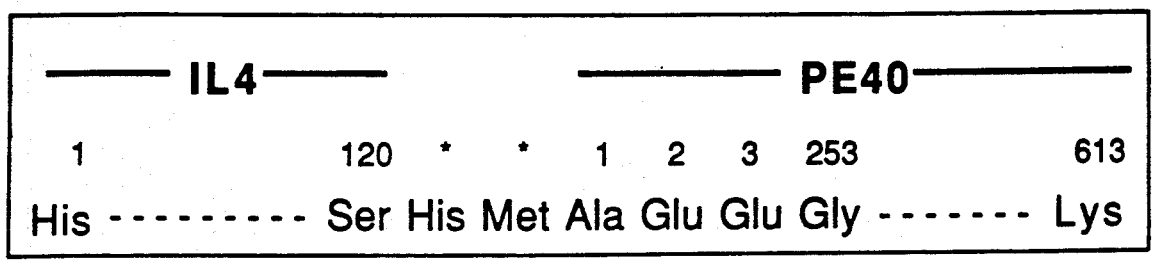

FIG. 1(B) shows abbreviated amino acid sequence of IL4-PE40.

Two amino acids (*) are added between IL4 and PE40 to create a NdeI site.

FIG. 2 demonstrates the localization of IL4-PE40 in *E. coli* BL21 (λDE3).

*E. coli* BL21 (λDE3) cells were transformed by plasmid pM048 and were processed as described in Materials and Methods. (A) Coomassie stained gel. (B) Immunoblotting with rabbit anti-PE antibody: lane 1, total cell pellet (nontransformed cells); lane 2, total cell pellet (transformed cells); lane 3, culture medium; lane 4, periplasm; lane 5, cytoplasm; lane 6, inclusion bodies. Molecular weights are indicated as $Mr \times 10^{-3}$. The arrow shows the new protein migrating at 53 kDa.

Figure 3A:
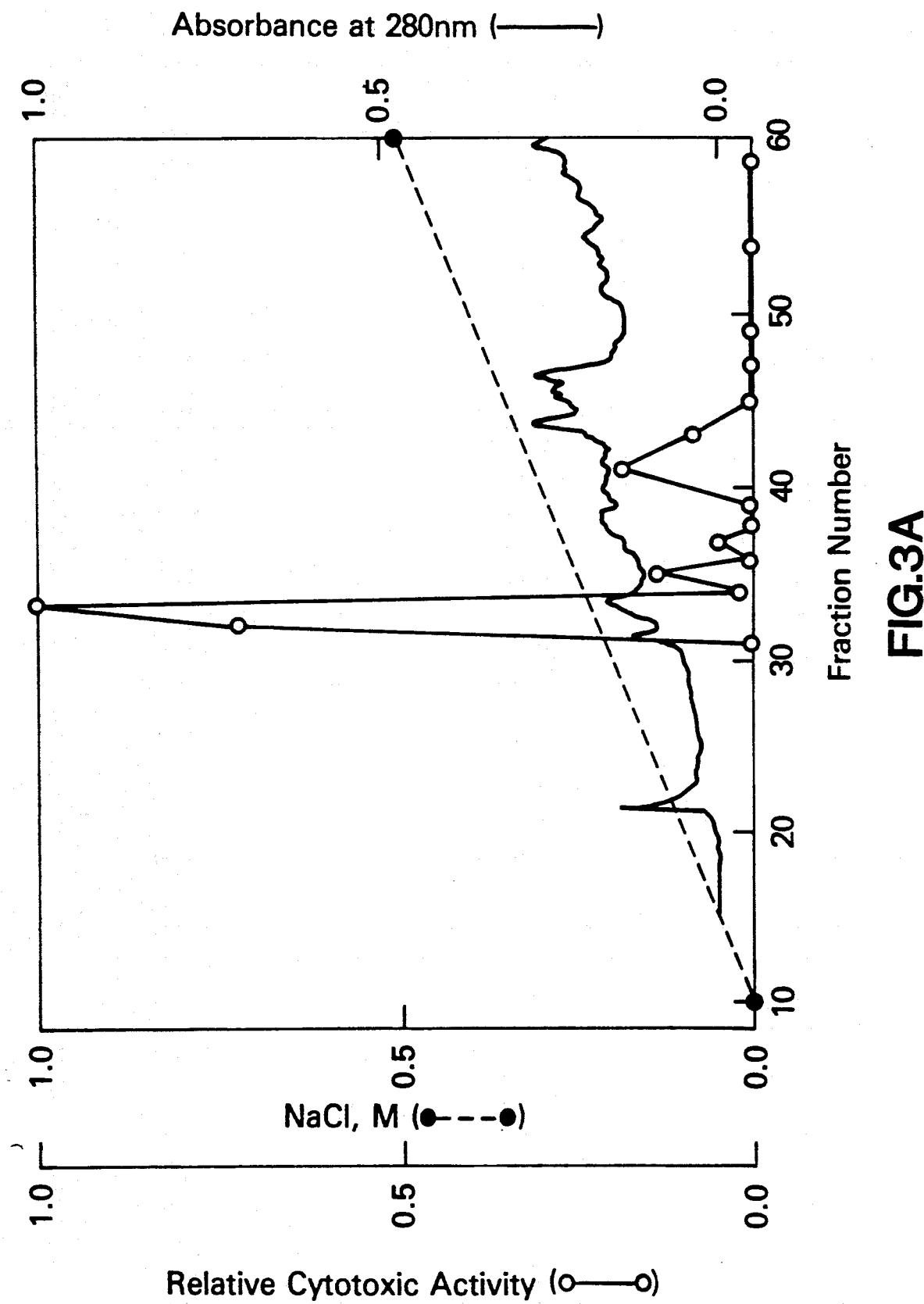

FIG. 3(A) shows the results of Mono Q ion exchange chromatography of IL4-PE40; inclusion bodies from a 750 ml culture of *E. coli* BL21 (λDE3) were processed as described in the text and then applied to a Mono Q column and 4 ml fractions were collected.

Figure 3B:
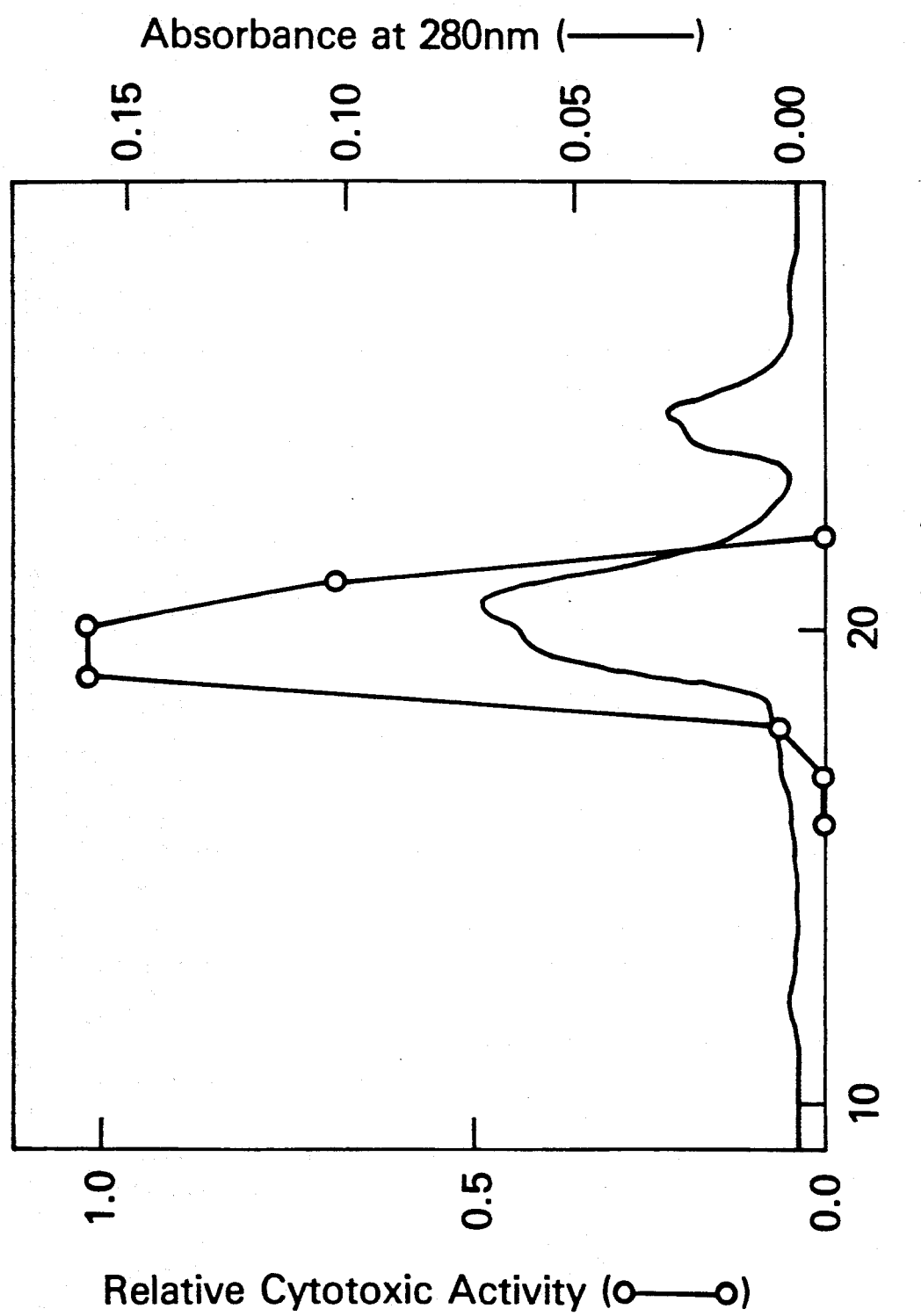

FIG. 3(B) shows the results of TSK-G3000 gel filtration chromatography of active material from Mono Q column; fraction 33 of the Mono Q column (220 μg of protein) was applied to a TSK-G3000 and 0.5 ml fractions were collected. In FIGS. 3(A) and (B), cytotoxic activity (○—○) is expressed as the relative ratio of peak activities from protein synthesis inhibition assays using CT.4R cells. Absorbance at 280 nm (—) was measured.

Figures 3C, 3D:
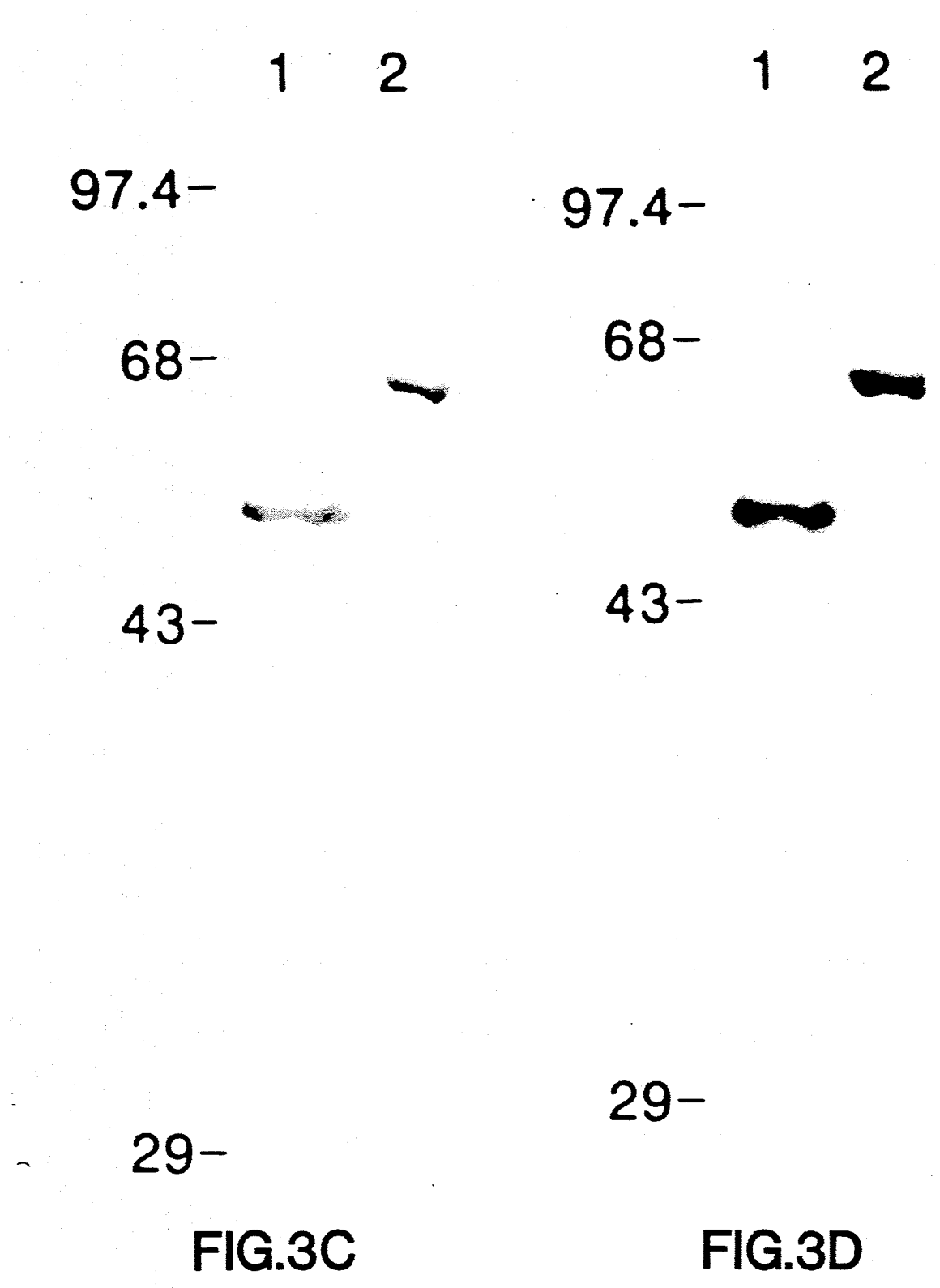

FIGS. 3(C) and (D) show the results of SDS/PAGE of purified IL4-PE40; TSK-G3000 purified material was subjected to SDS/PAGE. (C) Coomassie stained gel. (D) Immunoblotting with rabbit anti-PE antibody. Lane 1, fraction 19 of TSK-G3000 column; lane 2, PE. Molecular weights are indicated as $Mr \times 10^{-3}$.

Figure 4:
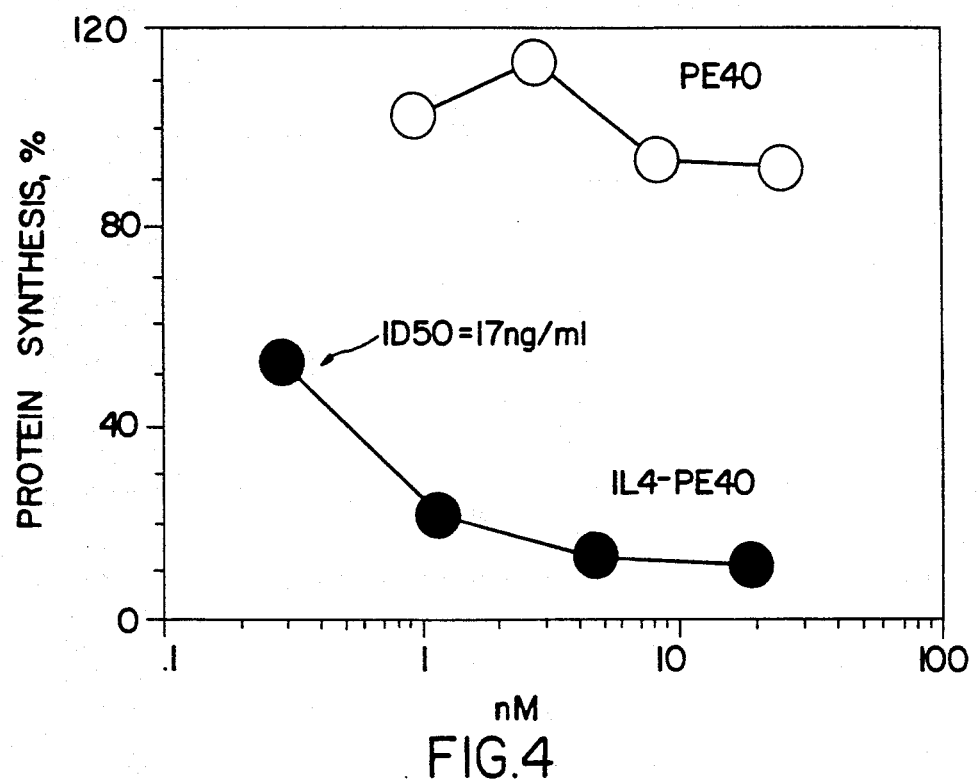

FIG. 4 demonstrates protein synthesis inhibition by IL4-PE40. CT.4R cells ($8 \times 10^3$ in 200 μl) were incubated in the culture medium containing IL2 (500 u/ml) with IL4-PE40 (●) or PE40 (*) or with no toxin. After a 40 hr incubation, [$^3$H]leucine incorporation into cellular protein was measured. Results are expressed as the percent of the value of cells incubated without toxin.

Figure 5:
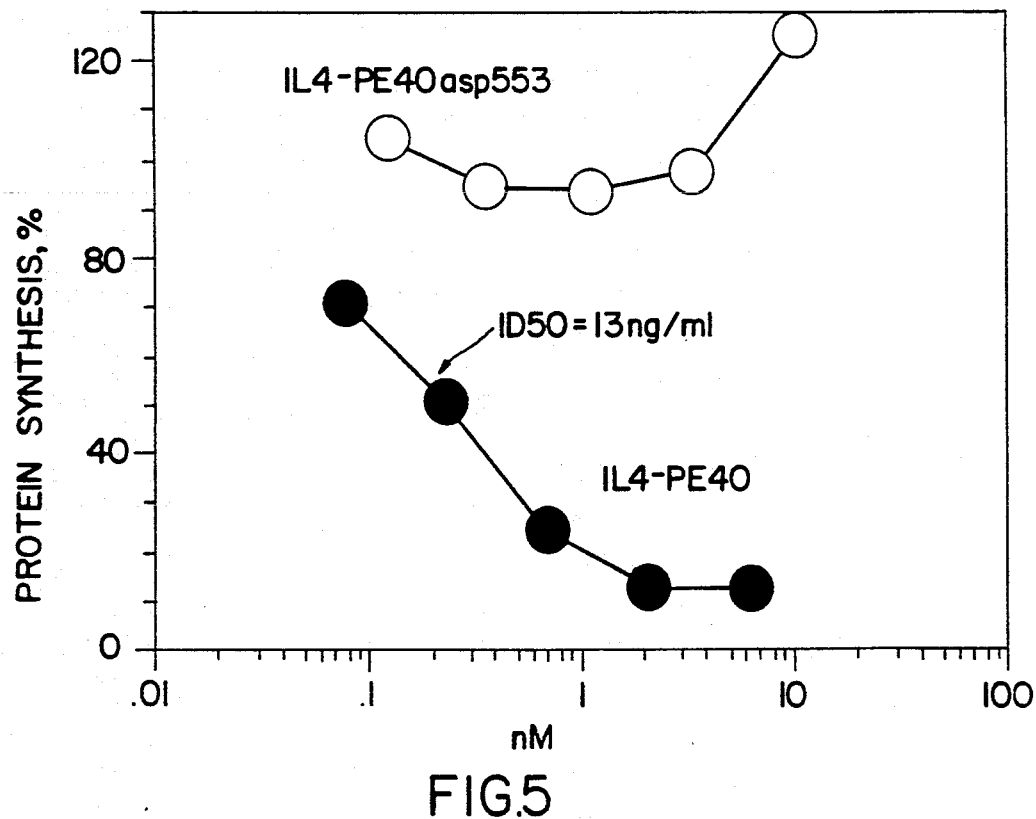

FIG. 5 shows the comparison of cytotoxic effects of IL4-PE40 and IL4-PE40 asp$^{553}$. CT.4R cells ($8 \times 10^3$ in 200 μl) were incubated in culture medium containing IL2 (500 u/ml) containing no additions (control) or various concentrations of IL4-PE40 (●) or IL4-PE40 asp$^{553}$ (○). After a 40 hr incubation, protein synthesis was measured.

Figure 6:
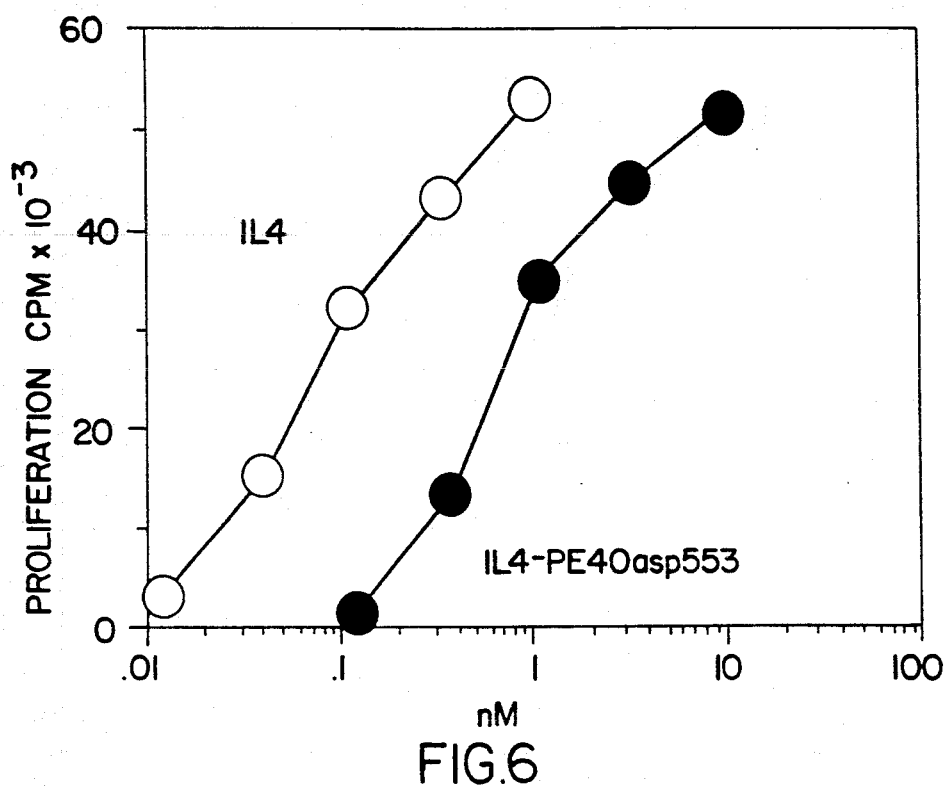

FIG. 6 demonstrates the mitogenic effect of IL4-PE40 asp$^{553}$ (●). After a 40 hr incubation, [$^3$H]thymidine incorporation was measured.

Figure 7:
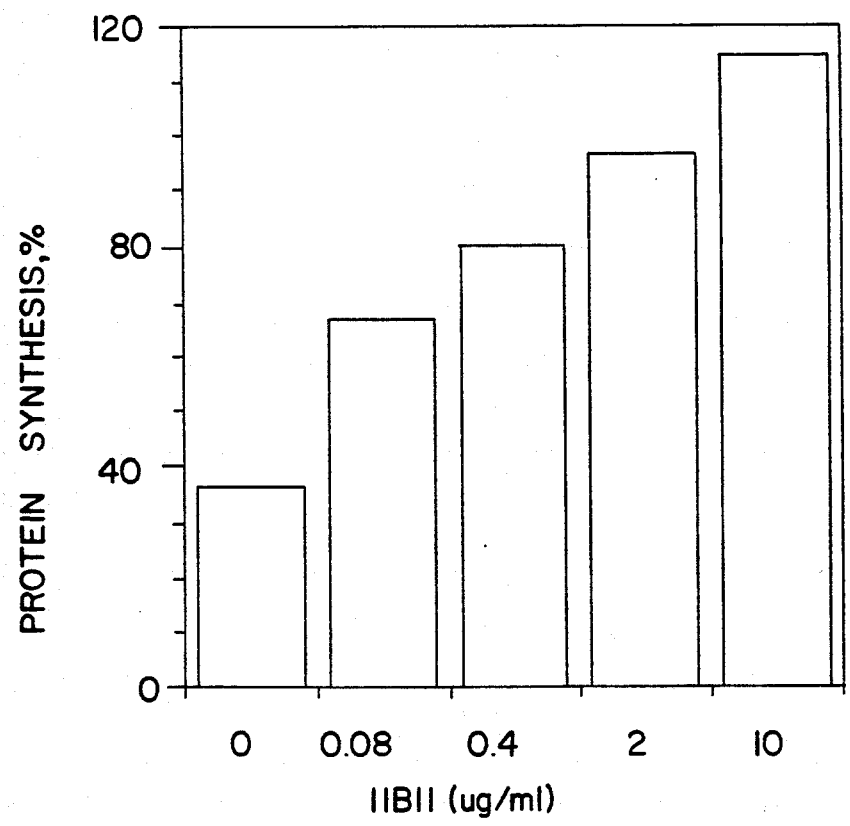

FIG. 7 demonstrates the neutralization of IL4-PE40 by an anti-IL4 monoclonal antibody. CT.4R cells ($8 \times 10^3$ cells in 200 μl) were incubated in culture medium containing IL2 (500 u/ml) and IL4-PE40 (1.9 nM) with various amount of anti-IL4 monoclonal antibody (11B11). After 20 hr incubation, protein synthesis was measured. The protein synthesis level without antibody was 35.8% of control.

Figure 8:
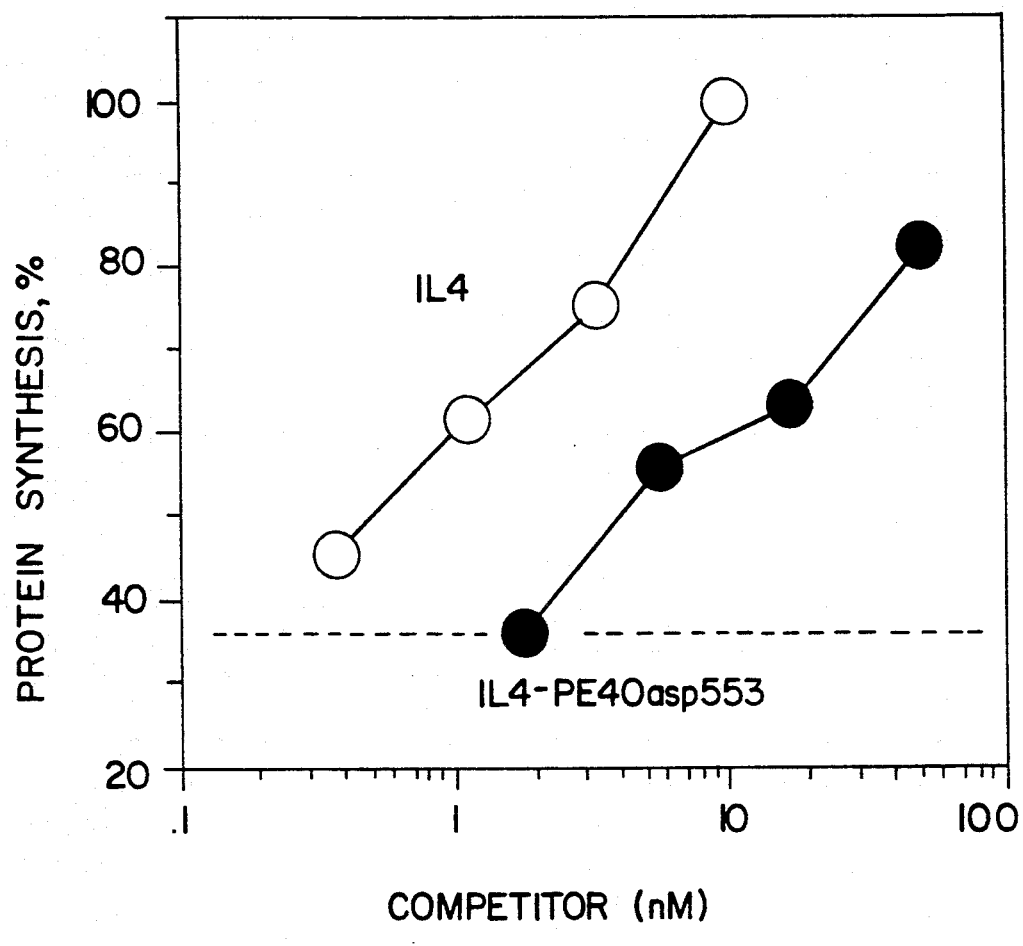

FIG. 8 shows the reversal of the cytotoxic activity of IL4-PE40 by IL4 or IL4-PE40 asp$^{553}$. CT.4R cells ($8 \times 10^3$ cells in 200 μl) were incubated in culture medium containing IL2 (500 u/ml) and IL4-PE40 (1.9 nM) with various amounts of competitors (○: IL4, ●: IL4-PE40 asp$^{553}$). After 20 hr incubation, protein synthesis was measured. The protein synthesis level without competitor (dotted line) was 36% of control.

DETAILED DESCRIPTION OF THE INVENTION

Various objects and advantages of the present invention are achieved by the plasmid pM048 which directs the synthesis of chimeric protein IL4-PE40 in a suitable expression vector and by a composition comprising said IL4-PE40 in a pharmaceutically acceptable carrier to selectively kill cells bearing IL4 receptors, without killing cells which do not express IL4 receptors.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed herein are standard methodologies well known to one of ordinary skill in the art.

MATERIALS AND METHODS

Reagents

Unless mentioned otherwise, all chemicals and enzymes were of analytical grade and purchased from commercial sources. For polymerase chain reaction (PCR), DNA amplification reagent kit (#N801-0043) from Perkin Elmer Cetus, Norwalk, Conn. was used. Anti-IL4 monoclonal antibody, 11B11 was purchased from Tex Star Monoclonals, Dallas, Tex. Recombinant murine IL4 was obtained from Dr. W. E. Paul, NIH, Bethesda, Md.

Plasmids, bacterial strains and cell lines

Plasmid pVC8f(+)T, which carried domain II and III of the PE gene (PE40) from pVC8, a T7 transcription terminator at the end of PE40 gene, and a fl origin of replication was derived from pVC4f(+)T as follows. A 3.4 Kb XbaI-BamH1 fragment from pVC45f(+)T was ligated to a 0.8 Kb XbaI-Bam H1 fragment of pVC 8. The plasmid carrying murine IL4 cDNA was obtained from Dr. S. Gillis (Immunex Co.). Plasmid pVC45M, which carried a gene for PE with an $asp^{553}$ mutation (ADP-ribosylating mutant), was constructed as described in Jinno et al (J. Biol. Chem. 263:13203–13207, 1988). The plasmid carrying fusion genes were expressed by IPTG induction in E. coli BL21 ($\lambda$DE3) as described by Siegall et al (1988, Proc. Natl. Acad. Sci. U.S.A. 85:9738–9742). CT.4R is a IL4 dependent murine T cell line expressing about 15,000 IL4 receptors. HUT102 is a human T cell leukemia and obtained from Dr. T. A. Waldmann (NCI). CTLL is a IL2 dependent murine T cell line and obtained from Dr. W. Paul (NIH). P815 is a murine mastocytoma cell line. P3X63-Ag8.653 is a clone derived from murine plasmacytoma, MOPC-21, and obtained from ATCC. NIH 3T3, Swiss 3T3 and L929 are murine fibroblast cell lines. A431 and KB are human epidermoid carcinoma cell lines.

Plasmid construction

Plasmid DNA was prepared and oligonucleotides were synthesized as described by Lorberboum-Galski et al (1988, Proc. Natl. Acad. Sci. U.S.A. 85:1922–1926). The chimeric gene encoding IL4-PE40 under the control of the T7 promoter was constructed as shown schematically in FIG. 1. First, NdeI site as created in the 5' and 3' end of IL4 coding sequence by polymerase chain reaction (PCR) using primers with recognition site for NdeI. As shown in FIG. 1, two oligonucleotide primers were synthesized; primer 1 is complementary to the 3' region of anti-sense strand of IL4 cDNA and primer 2 is complementary to the 3' region of sense strand. In both primers, 5 bases are changed to create NdeI sites. After 25 cycles of PCR using primer 1 and 2 (1 $\mu$M) and a 0.55 kb BamHI-EcoRI DNA fragment (0.1 ng/reaction) that contained the IL4 coding sequence as template, a 0.406 kb DNA fragment was amplified. After separation on a low melting point agarose gel, the 0.406 kb DNA was eluted, then cut with NdeI, and the 0.366 kb fragment was separated. The 0.366 kb NdeI fragment was subcloned into the NdeI site of pVC8f(+)T. The resulting plasmid had a 0.366 kb IL4 coding gene in two orientations at the 5' end of the PE40 gene. After restriction analysis, a plasmid with the IL4 in the proper orientation with respect to the PE40 gene was identified (pM048). Plasmid pM048M (IL4-PE40 $asp^{553}$) was constructed by cleaving pM048 with BamHI and EcoRI and replacing the 0.46 kb fragment with a similar BamHI-EcoRI fragment from pVC45M (Jinno et al, 1988, J. Biol. Chem. 263:13203–13207).

A deposit of plasmid pM048 has been made at the ATCC, Rockville, Md. on May 5, 1989 under the accession number 67946. The deposit shall be viably maintained, replacing if it becomes non-viable during the life of the patent, for a period of 30 years from the date of the deposit, or for 5 years from the last date of request for a sample of the deposit, whichever is longer, and made available to the public without restriction in accordance with the provisions of the law. The Commissioner of Patents and Trademarks, upon request, shall have access to the deposit.

Expression and localization of IL4-PE40

E. coli BL21 ($\lambda$DE3) cells were transformed with the plasmid pM048, cultured in 1 liter LB broth, with ampicillin (100 $\mu$g/ml) for 90 min with 1 mM isopropyl $\beta$-D-thiogalactoside when $OD_{650}$ value reached 0.5. The separation of different compartments of cells was done as described by Siegall et al, supra.

Gel electrophoresis and immunoblotting

SDS-PAGE on 10% gels was performed as described by Laemmli (1970, Nature 227:680–685). The gels were stained with Coomassie blue. For immunoblotting, electrophoresed samples were transferred to nitrocellulose paper and processed using rabbit anti-PE-anti-serum as described by Hwang et al (1987, Cell 48:129–136).

Purification of IL4-PE40

For purification of IL4-PE40, the pellet containing inclusion bodies was prepared by centrifugating the sonicated spheroplast (Siegall et al, supra). The pellet, containing IL4-PE40, was denatured in extraction buffer (7M guanidine-HCl, 100 mM Tris-HCl pH 8.0., 5 mM EDTA). After centrifugation at 40,000 rpm for 15 min, the supernatant containing denatured protein was rapidly diluted in 80 volumes of PBS, allowed to sit for 16 hr at 4° C. for renaturation. After dialyzing against 20 mM Tris (pH 8.0), 1 mM EDTA, the samples were applied onto Mono Q column (10×100 mm) and eluted with 200 ml linear gradient of NaCl (0–500 mM in 20 m Tris, pH 8.0, 1 mM EDTA); 4 ml fractions were collected and absorbance at 280 nM was monitored. The fraction containing the peak cytotoxic activity on CT.4R cells (fraction 33) was applied onto a TSK G3000 (7.8×300 mm) gel filtration column and eluted with 0.2M sodium phosphate (pH 7.0) containing 1 mM EDTA. The chimeric mutant protein, IL4-PE40 $asp^{553}$ was expressed and purified the same way as for IL4-PE40. It also had the same MW as determined by SDS-PAGE (data not shown).

Protein synthesis inhibition assays

The cytotoxic activity of IL4-PE40 was tested on CT.4R cells. CT.4R cells were maintained in the RPMI 1640 medium containing 5% FCS; 50 $\mu$M of 2-mercaptoethanol, 1 mM of sodium pyruvate, 50 u/ml of penicillin, 50 $\mu$g/ml of streptomycin, 50 $\mu$g/ml of gentamycin and 500 u/ml of murine IL4. For assay, cells were washed to remove IL4 and plated in 96 well tissue culture plate at $8 \times 10^3$ cells in 100 $\mu$l. Then various concentrations of IL4-PE40 were added. 500 u/ml of IL2 was also added to keep the cells growing during the assay period. For blocking or neutralizing experiments, IL4-PE40 was pre-mixed with competitors or neutralizing antibodies and then added to the cells. After a 1 or 2 day incubation at 37° C., cells were cultured with 2 μCi of [$^3$H]-leucine for 4 hr, and the radioactivity incorporated into cells was measured by standard procedures (Ogata et al, 1988, *J. Immunol.* 141:4224–4228). When IL4-PE40 was tested on CTLL cells, the same protocol was used. For other cell lines, culture medium without IL2 and different cell numbers were used (HUT102, and P3X63-Ag8.653, $1 \times 10^4$ cells/well; NIH3T3, Swiss 3T3, L929, A431, and KB, $1.6 \times 10^4$/well; P815, $8 \times 10^3$ cells/well).

Mitogenic assay

CT.4R cells ($5 \times 10^3$ cells in 200 μl) were cultured in the absence or presence of various amounts of rIL4 or IL4-PE40 asp$^{553}$. After a 40 hr incubation, cells were incubated with [$^3$H]thymidine (0.5 μCi) for 6 hrs and radioactivity incorporated into cells was measured.

RESULTS

Construction of expression plasmid encoding IL4-PE40

A DNA fragment encoding murine IL4 was subcloned into the NdeI site of pVC8f(+)T (FIG. 1A). To accomplish this, NdeI sites were created in the 5' and 3' end of the IL4 coding sequence by polymerase chain reaction (PCR) using primers with recognition sites for NdeI as described herein supra. As indicated in FIG. 1, primer 1 is complementary to the 3' region of anti-sense strand. Primer 2 is complementary to the 3' region of sense strand. In both primers, 5 bases are changed to create NdeI sites. After 25 cycles of PCR with these primers and a DNA fragment that contained the IL4 coding sequence, the amplified DNA fragment acquired NdeI sites at both ends.

The resulting plasmid, pM048 expressed under the control of a bacteriophage T7 late promoter. The recombinant chimeric protein, IL4-PE40 thus synthesized, is composed of 486 amino acids in which a native IL4 sequence of 120 amino acids is followed by amino acids, his, met and 1-3 and 253-613 of PE (FIG. 1B).

Expression of IL4-PE40

To express IL4-PE40, *E. coli* BL21 (λDE3) cells were transformed with plasmid pM048. After induction with IPTG, the cells were collected and processed as described herein supra. The new protein, migrating at 53 k Da, was readily detectable on SDS PAGE of the total cell pellet (FIG. 2A). The size of this protein corresponds to the expected size for IL4-PE40 and immunoblotting analysis showed that this protein reacted with anti-PE antibody (FIG. 2B). The culture supernatant or the periplasm had negligible amounts of this protein. Separation of sonicated spheroplasts into cytoplasm and a pellet that contained inclusion bodies showed that the 53 k Da protein was mostly retained in the inclusion bodies.

Purification of IL4-PE40

To prepare purified IL4-PE40, the inclusion bodies were denatured in 7M guanidine and then renatured as described in the Materials and Methods. The renatured protein was applied to Mono Q ion-exchange column (FIG. 3A). Fraction 33 from the Mono Q column showed high cytotoxic activity on IL4 receptor bearing cells and was applied to a TSK-G3000 gel filtration column (FIG. 3B). Most of the cytotoxic activity came in fractions 19 and 20 (FIG. 3B). As shown in FIG. 3C, fraction 19 of the TSK-G3000 column contained a 53 kDa protein that was substantially pure (about 90%) and this protein reacted with anti-PE antibody (FIG. 3D). This protein also had almost the same ADP-ribosyltransferase activity as an equal amount of PE40 (data not shown).

Protein synthesis inhibition by IL4-PE40

To test the cytotoxic activity of IL4-PE40, a murine T cell line, CT.4R, which expresses around 15,000 IL4-receptors was used. This cell line can grow in the presence of either IL4 or IL2 and was maintained in culture medium containing recombinant murine IL4.

CT.4R cells were cultured with various amounts of IL4-PE40. IL2 (500 u/ml) was added to the culture to keep CT.4R cells growing during the assay period. After two days, the level of protein synthesis was determined. As shown in FIG. 4, IL4-PE40 inhibited protein synthesis in CT.4R cells in a concentration-dependent manner. The concentration of IL4-PE40 giving a 50% reduction of protein synthesis (ID$_{50}$) was about 17 ng/ml. Conversely, the non-chimeric protein, PE40, which cannot bind to the IL4 receptor, had little or no effect on protein synthesis (ID$_{50} > 1,000$ ng/ml).

CT.4R cells were chosen since they are known to have relatively large number of IL4 receptors. To test cells of B-cell lineage, a murine myeloma P3X63-Ag8.653 was also tested and found to be sensitive with ID$_{50}$ of about 12 ng/ml (Table 1).

ADP-ribosylation activity is essential for the cytotoxic effect of IL4-PE40

The nature of the cytotoxic effect of IL4-PE40 was further investigated by determining the cytotoxicity of IL4-PE40 asp$^{553}$, a mutant form of the chimeric protein that has very low ADP-ribosylation activity. As shown in FIG. 5, IL4-PE40 asp$^{553}$ was found not to have any cytotoxic effect up to a concentration of 1000 ng/ml. Rather than inhibiting the synthesis of protein by CT.4R cells, IL4-PE40 asp$^{553}$ displayed mitogenic activity similar to that of IL4 (FIG. 6). Although the mitogenic activity of IL4-PE40 asp$^{553}$ was about 10-fold less than that of IL4, this result clearly showed that the IL4-toxin retained substantial binding activity toward IL4 receptors.

IL4-receptor mediated cytotoxicity by IL4-PE40

To demonstrate further that the cytotoxic activity of IL4-PE40 was mediated by the IL4-receptor, two other approaches were used. First, the neutralizing effect of anti-IL4 antibody, 11B11, on IL4-PE40 was examined. 11B11 is a monoclonal antibody that can bind to IL4 and inhibit IL4 binding to the IL4-receptor (Ohara et al, 1987, *Nature* [London] 325:537–540). As shown in FIG. 7, 11B11 neutralized the cytotoxic effect of IL4-PE40.

The second approach involved competing the cytotoxic activity of IL4-PE40 with either IL4 or IL4-PE40 asp$^{553}$. Both IL4 and IL4-PE40 asp$^{553}$ blocked the cytotoxic effect of IL4-PE40 (FIG. 8). IL4 was about 10-fold more effective in blocking the cytotoxic effect of IL4-PE40 than IL4-PE40 asp$^{553}$. These results clearly showed that the binding of IL4-PE40 to IL4 receptors is essential for its cytotoxic effect.

Cytotoxic effect of IL4-PE40 on various cell lines

The effect of IL4-PE40 on cell lines lacking receptor for murine IL4 was examined to demonstrate further the specifically of the cytotoxic effect. HUT102 is a human T cell leukemia cell line. It is well known that murine IL4 does not bind to human cells (Ohara et al, supra; Park et al, 1987, *Proc. Natl. Acad. Sci. U.S.A.* 84:1669–1673). Therefore, this cell line was first tested because it had been shown previously to be sensitive to another chimeric toxin, IL2-PE40 (Lorberboum et al, 1988, *Proc. Natl. Acad. Sci. U.S.A.* 85:1922–1926). As shown in Table 1, IL4-PE40 had very little or no cytotoxic effect on HUT102 cells ($ID_{50}>1000$ ng/ml). Two other human cell lines, A431 and KB, were also tested and IL4-PE40 was found not to be cytotoxic to them. On the contrary, IL4-PE40 was cytotoxic to murine cell lines, CTLL (a T cell line) and P815 (a mastocytoma cell line), which had been reported to possess IL4 receptors (Ohara et al, supra; Park et al, supra). IL4-PE40 was also cytotoxic to a murine myeloma cell line, P3X63-Ag8.653. IL4-PE40 had weak cytotoxic effects on two murine fibroblast cell lines, Swiss 3T3 and L929, but had little or not effect on NIH 3T3. The cytotoxic activity of IL4-PE40 to CTLL, P815, Swiss 3T3 and L929 was neutralized by anti-IL4 antibodies (11B11) (data not shown). IL4-PE40 asp$^{553}$ or PE40, lacking ADP-ribosylating activity or cell binding domain respectively, had very low effects on all the cell lines listed in Table 1. These results confirm the specific cytotoxicity of IL4-PE40.

The availability of IL4-PE40 now makes it possible to suppress immune response. It has been reported that activation of B and T cells with mitogen or anti-IgM antibody produces a 5- to 10-fold increase in IL4-receptor number (Park et al, 1987, *J. Exp. Med.* 166:476–488). Hence IL4-PE40 could be utilized for immuno-suppression by depleting activated lymphocytes. IL4-PE40 could also be used for the treatment of certain tumors because it has been reported that certain tumor cell lines derived from B-lymphomas, T-Leukemias, mastocytomas and the like have relatively high number of IL4-receptors (Ohara et al, supra).

It is understood that the examples and embodiments described herein are for illustrative purposes only and that various modifications or changes in light thereof will be suggested to persons skilled in the art and are to be included within the spirit and purview of this application and scope of the appended claims.

TABLE I

| | CYTOTOXIC ACTIVITY OF IL4-PE40 | | | |
| --- | --- | --- | --- | --- |
| | $ID_{50}$, ng/ml | | | |
| Cell LINE | IL4-PE40 | IL4-PE40 asp$^{553}$ | PE | PE40 |
| CT.4R | 17 | >1000 | >250 | >1000 |
| CTLL | 250 | >1000 | 80 | 1000 |
| P3X63-Ag8.653 | 12 | >1000 | N.D. | >1000 |
| P815 | 20 | >1000 | 59 | >1000 |
| NIH3T3 | >1000 | >1000 | 0.86 | >1000 |
| Swiss3T3 | 420 | >1000 | 0.16 | >1000 |
| L929 | 350 | >1000 | 0.16 | >1000 |
| HUT102 | >1000 | N.D. | 3.4 | N.D. |
| A431 | >1000 | N.D. | 1.2 | N.D. |
| KB | >1000 | N.D. | 29 | N.D. |

The $ID_{50}$ was calculated from protein synthesis inhibition assays measuring [$^3$H]leucine incorporation after two days incubation with toxin. N.D.: not done.

What is claimed is:

1. A functionally active recombinant IL-4-PE40 fusion protein that selectively kills cells bearing IL-4 receptors, without killing cells lacking IL-4 receptors, wherein the fusion protein has ADP ribosylating properties.

2. The recombinant fusion protein of claim 1 produced by employing plasmid pM048 in an expression vector.

3. A composition, comprising an effective amount of the recombinant fusion protein of claim 1 and pharmaceutically acceptable carrier.

4. A mutant form of the fusion protein of claim 1 which consist of IL-4-PE40 Asp$^{553}$.

* * * * *